US011941534B2

(12) United States Patent
Kalsi et al.

(10) Patent No.: US 11,941,534 B2
(45) Date of Patent: Mar. 26, 2024

(54) GENOME SEQUENCE ALIGNMENT SYSTEM AND METHOD

(71) Applicant: Intel Corporation, Santa Clara, CA (US)

(72) Inventors: Gurpreet Singh Kalsi, Bangalore (IN); Anant V. Nori, Bangalore (IN); Christopher Justin Hughes, Santa Clara, CA (US); Sreenivas Subramoney, Bangalore (IN); Damla Senol, Pittsburg, PA (US)

(73) Assignee: Intel Corporation, Santa Clara, CA (US)

( * ) Notice: Subject to any disclaimer, the term of this patent is extended or adjusted under 35 U.S.C. 154(b) by 894 days.

(21) Appl. No.: 16/729,379

(22) Filed: Dec. 28, 2019

(65) Prior Publication Data
US 2021/0201163 A1    Jul. 1, 2021

(51) Int. Cl.
*G06N 3/123*    (2023.01)
*G06F 9/30*    (2018.01)
*G06F 15/78*    (2006.01)
*G06F 15/80*    (2006.01)
*G06F 40/45*    (2020.01)
*G16B 30/00*    (2019.01)
*G16B 30/10*    (2019.01)
*G06F 17/00*    (2019.01)

(52) U.S. Cl.
CPC ......... *G06N 3/123* (2013.01); *G06F 9/30036* (2013.01); *G06F 15/78* (2013.01); *G06F 15/8053* (2013.01); *G06F 15/8061* (2013.01); *G06F 40/45* (2020.01); *G16B 30/00* (2019.02); *G16B 30/10* (2019.02); *G06F 17/00* (2013.01)

(58) Field of Classification Search
CPC ..... G06N 3/123; G06F 9/30036; G06F 15/78; G06F 15/8053; G06F 15/8061; G06F 40/45; G06F 17/00; G16B 30/00; G16B 30/10
See application file for complete search history.

(56) References Cited

U.S. PATENT DOCUMENTS 5,724,253 A * 3/1998 Skovira .................. G16B 30/00
435/6.1

FOREIGN PATENT DOCUMENTS

JP    2012-32975    *    2/2012

OTHER PUBLICATIONS

JP 2012-32975—Machine translation in English—published Feb. 16, 2012, pp. 1-16 (Year: 2012).*

Smith, Temple F., and Michael S. Waterman. "Comparison of biosequences." Advances in applied mathematics 2.4 (1981): 482-489.
Myers, Gene. "A fast bit-vector algorithm for approximate string matching based on dynamic programming." Journal of the ACM 46.3 (1999): 395-415.
Baeza-Yates, Ricardo, and Gaston H. Gonnet. "A new approach to text searching." Communications of the ACM 35.10 (1992): 74-82.
Wu, Sun, and Udi Manber. "Fast text search allowing errors." Communications of the ACM 35.10 (1992): 83-91.
Y. Turakhia, G. Bejerano, and W. J. Dally, "Darwin: A genomics co-processor provides up to 15,000 × acceleration on long read assembly," in Proceedings of the Twenty-Third International Conference on Architectural Support for Programming Languages and Operating Systems, pp. 199-213, ACM, 2018.
D. Fujiki, A. Subramaniyan, T. Zhang, Y. Zeng, R. Das, D. Blaauw, and S. Narayanasamy, "GenAx: A Genome Sequencing Accelerator," in Proceedings of the International Symposium on Computer Architecture (ISCA), 2018.
Yatish Turakhia et.al "Darwin-WGA: A Co-processor Provides Increased Sensitivity in Whole Genome Alignments with High Speedup" 2019 IEEE International Symposium on High Performance Computer Architecture (HPCA).
Oxford Nanopore Technologies. [Online]. Available: https://nanoporetech.com.
Pacific Biosciences (PacBio). [Online]. Available: https://www.pacb.com.
S. H. Pugsley, J. Jestes, H. Zhang, R. Balasubramonian, V. Srinivasan, A. Buyuktosunoglu, A. Davis, and F. Li, "NDC: Analyzing the impact of 3D-stacked memory + logic devices on MapReduce workloads," in 2014 IEEE International Symposium on Performance Analysis of Systems and Software (ISPASS). IEEE, 2014, pp. 190-200.
M. A. Quail, M. Smith, P. Coupland, T. D. Otto, S. R. Harris, T. R. Connor, A. Bertoni, H. P. Swerdlow, and Y. Gu, "A tale of three next generation sequencing platforms: comparison of Ion Torrent, Pacific Biosciences and Illumina MiSeq sequencers," BMC Genomics, vol. 13, No. 1, p. 341, 2012.
P. Shivakumar and N. P. Jouppi, "Cacti 3.0: An integrated cache timing, power, and area model," 2001.

(Continued)

*Primary Examiner* — Narayan K Bhat
(74) *Attorney, Agent, or Firm* — Fletcher Yoder, PC

(57) ABSTRACT

A system is provided that includes a bit vector-based distance counter circuitry configured to generate one or more bit vectors encoded with information about potential matches and edits between a read and a reference genome, wherein the read comprises an encoding of a fragment of deoxyribonucleic acid (DNA) encoded via bases G, A, T, C. The system further includes a bit vector-based traceback circuitry configured to divide the reference genome into one or more windows and to use the plurality of bit vectors to generate a traceback output for each of the one or more windows, wherein the traceback output comprises a match, a substitution, an insert, a delete, or a combination thereof, between the read and the one or more windows.

20 Claims, 9 Drawing Sheets

(56) References Cited

OTHER PUBLICATIONS

T. F. Smith, M. S. Waterman et al., "Identification of Common Molecular Subsequences," Journal of Molecular Biology, 1981.
M. Šošić and M. Šikić, "Edlib: a C/C++ library for fast, exact sequence alignment using edit distance," Bioinformatics, vol. 33, No. 9, pp. 1394-1395, 2017.
K. Tang, O. Kislal, M. Kandemir, and M. Karakoy, "Data Movement Aware Computation Partitioning," in MICRO, 2017.
P.- A. Tsai, C. Chen, and D. Sanchez, "Adaptive Scheduling for Systems with Asymmetric Memory Hierarchies," in MICRO-51, 2018.
P.- A. Tsai, C. Chen, and D. Sanchez, "Adaptive scheduling for systems with asymmetric memory hierarchies," in 2018 51st Annual IEEE/ACM International Symposium on Microarchitecture (MICRO). IEEE, 2018, pp. 641-654.
Y. Turakhia, S. D. Goenka, G. Bejerano, and W. J. Dally, "Darwinwga: A co-processor provides increased sensitivity In whole genome alignments with high speedup," in HPCA, 2019.
Y. Turakhia, G. Bejerano, and W. J. Dally, "Darwin: A genomics co-processor provides up to 15,000x acceleration on long read assembly," in ASPLOS, 2018.
J. L. Weirather, M. de Cesare, Y. Wang, P. Piazza, V. Sebastiano, X.-J. Wang, D. Buck, and K. F. Au, "Comprehensive comparison of pacific biosciences and oxford nanopore technologies and their applications to transcriptome analysis," F1000Research, 2017.
S. J. Wilton and N. P. Jouppi, "CACTI: An enhanced cache access and cycle time model," IEEE Journal of Solid-State Circuits, vol. 31, No. 5, pp. 677-688, 1996.
S. Wu and U. Manber, "Fast text searching allowing errors," Communications of the ACM, vol. 35, No. 10, pp. 83-92, 1992.
C. Xie, S. L. Song, J. Wang, W. Zhang, and X. Fu, "Processing-in-Memory Enabled Graphics Processors for 3D Rendering," in HPCA, 2017.
H. Xin, J. Greth, J. Emmons, G. Pekhimenko, C. Kingsford, C. Alkan, and O. Mutlu, "Shifted Hamming distance: a fast and accurate SIMD-friendly filter to accelerate alignment verification in read mapping," Bioinformatics, vol. 31, No. 10, pp. 1553-1560, May 2015.
H. Xin, D. Lee, F. Hormozdiari, S. Yedkar, O. Mutlu, and C. Alkan, "Accelerating read mapping with FastHASH," BMC Genomics, vol. 14, No. 1, p. S13, Jan. 2013.
M. Zhang, Y. Zhuo, C. Wang, M. Gao, Y. Wu, K. Chen, C. Kozyrakis, and X. Qian, "GraphP: Reducing Communication for PIM-Based Graph Processing with Efficient Data Partition," in HPCA, 2018.
ARM Cortex-A7. [Online]. Available: https://developer.arm.com/ip-products/processors/cortex-a/cortex-a7.
"Intel performance counter monitor." [Online]. Available: https://software.intel.com/en-US/articles/intel-performance- counter-monitor.
NCBI: GRCh38.p13. [Online]. Available:https://www.ncbi.nlm.nih.gov/assembly/GCA_000001405.28.
"Tool from Synopsys, Design Compiler (Version L-2016.03-SP2)." [Online]. Available: https://www.synopsys.com.
J. Ahn, S. Hong, S. Yoo, O. Mutlu, and K. Choi, "A Scalable Processing-in-Memory Accelerator for Parallel Graph Processing," in ISCA, 2015.
J. Ahn, S. Yoo, O. Mutlu, and K. Choi, "PIM-Enabled Instructions: A Low-Overhead, Locality-Aware Processing-in- Memory Architecture," in ISCA, 2015.
M. Alser, H. Hassan, A. Kumar, O. Mutlu, and C. Alkan, "Shouji: A Fast and Efficient Pre-Alignment Filter for Sequence Alignment," Bioinformatics, vol. btz234.
M. Alser, H. Hassan, H. Xin, O. Ergin, O. Mutlu, and C. Alkan, "GateKeeper: a new hardware architecture for accelerating prealignment in DNA short read mapping," Bioinformatics, 2017.
M. Alser, O. Mutlu, and C. Alkan, "MAGNET: Understanding and Improving the Accuracy of Genome Pre-Alignment Filtering," arXivpreprint arXiv:1707.01631, Jul. 2017.

M. J. Alvarez-Cubero, M. Saiz, B. Martinez-Garcia, S. M. Sayalero, C. Entrala, J. A. Lorente, and L. J. Martinez-Gonzalez, "Next generation sequencing: an application in forensic sciences?" Annals of human biology, vol. 44, No. 7, pp. 581-592, 2017.
S. Ardui, A. Ameur, J. R. Vermeesch, and M. S. Hestand, "Single Molecule Real-time (SMRT) Sequencing Comes of Age: Applications and Utilities for Medical Diagnostics," Nucleic Acids Research, 2018.
R. A. Baeza-Yates and G. H. Gonnet, "A New Approach to Text Searching," in ACM SIGIR Forum, 1989.
S. S. Banerjee, M. El-Hadedy, J. B. Lim, Z. T. Kalbarczyk, D. Chen, S. S. Lumetta, and R. K. Iyer, "ASAP: Accelerated Short-Read Alignment on Programmable Hardware," IEEE Transactions on Computers, 2019.
A. Boroumand, S. Ghose, M. Patel, H. Hassan, B. Lucia, K. Hsieh, K. T. Malladi, H. Zheng, and O. Mutlu, "LazyPIM: An Efficient Cache Coherence Mechanism for Processing-in-Memory," IEEE CAL, 2017.
A. Boroumand, S. Ghose, Y. Kim, R. Ausavarungnirun, E. Shiu, R. Thakur, D. Kim, A. Kuusela, A. Knies, P. Ranganathan, and O. Mutlu, "Google workloads for consumer devices: Mitigating data movement bottlenecks," in Proceedings of the Twenty-Third International Conference on Architectural Support for Programming Languages and Operating Systems. ACM, 2018, pp. 316-331.
D. S. Cali, J. S. Kim, S. Ghose, C. Alkan, and O. Mutlu, "Nanopore sequencing technology and tools for genome assembly: computational analysis of the current state, bottlenecks and future directions," Briefings in Bioinformatics, Apr. 2018. [Online]. Available:https://doi.org/10.1093/bib/bby017.
E. Check Hayden, "Technology: The 1,000 Genome," Nature News, 2014.
J. Daily, "Parasail: SIMD C library for global, semi-global, and local pairwise sequence alignments," BMC Bioinformatics, vol. 17, No. 1, p. 81, Dec. 2016.
Darwin: A co-processor for long read alignment. [Online]. Available:https://github.com/yatisht/darwin.
W. R. Davis, J. Wilson, S. Mick, J. Xu, H. Hua, C. Mineo, A. M. Sule, M. Steer, and P. D. Franzon, "Demystifying 3D ICs: The Pros and Cons of Going Vertical," IEEE Design & Test of Computers, 2005.
M. Drumond, A. Daglis, N. Mirzadeh, D. Ustiugov, J. Picorel, B. Falsafi, B. Grot, and D. Pnevmatikatos, "The mondrian data engine," in 2017 ACM/IEEE 44th Annual International Symposium on Computer Architecture (ISCA). IEEE, 2017, pp. 639-651.
K. Fei, Z. Dan, L. Lina, M. Xin, and Z. Chunlei, "FPGASW: Accelerating Large-Scale Smith-Waterman Sequence Alignment Application with Backtracking on FPGA Linear Systolic Array," Interdisciplinary Sciences: Computational Life Sciences, vol. 10, No. 1, pp. 176-188, Mar. 2018.
C. Firtina and C. Alkan, "On Genomic Repeats and Reproducibility," Bioinformatics, 2016.
D. Fujiki, A. Subramaniyan, T. Zhang, Y. Zeng, R. Das, D. Blaauw, and S. Narayanasamy, "GenAx: A genome sequencing accelerator," in ISCA, 2018.
M. Gao, G. Ayers, and C. Kozyrakis, "Practical Near-Data Processing for In-Memory Analytics Frameworks," in PACT, 2015.
M. Gao, J. Pu, X. Yang, M. Horowitz, and C. Kozyrakis, "TETRIS: Scalable and Efficient Neural Network Acceleration with 3D Memory," SIGARCH Comput. Archit. News, 2017.
E. Georganas, A. Buluc, J. Chapman, L. Oliker, D. Rokhsar, and K. Yelick, "merAligner: A Fully Parallel Sequence Aligner," in 2015 IEEE International Parallel and Distributed Processing Symposium. IEEE, May 2015, pp. 561-570.
T. C. Glenn, "Field Guide to Next-generation DNA Sequencers," Molecular Ecology Resources, 2011.
S. Goodwin, J. D. McPherson, and W. R. McCombie, "Coming of age: ten years of next-generation sequencing technologies," Nature Reviews Genetics, vol. 17, No. 6, p. 333, 2016.
M. Holtgrewe, "Mason—a read simulator for second generation sequencing data," Technical Report FU Berlin, 2010.
K. Hsieh, S. Khan, N. Vijaykumar, K. K. Chang, A. Boroumand, S. Ghose, and O. Mutlu, "Accelerating Pointer Chasing In 3D-Stacked Memory: Challenges, Mechanisms, Evaluation," in ICCD, 2016.

(56) References Cited

OTHER PUBLICATIONS

Hybrid Memory Cube Consortium, "HMC Specification 2.1," 2014.
Ilumina. [Online]. Available: https://www.illumina.com.
M. Jain, S. Koren, K. H. Miga, J. Quick, A. C. Rand, T. A. Sasani, J. R. Tyson, A. D. Beggs, A. T. Dilthey, I. T. Fiddes et al., "Nanopore sequencing and assembly of a human genome with ultra-long reads," Nature biotechnology, 2018.
M. Jain, J. R. Tyson, M. Loose, C. L. Ip, D. A. Eccles, J. O'Grady, S. Malla, R. M. Leggett, O. Wallerman, H. J. Jansen, V. Zulunin, E. Birney, B. L. Brown, T. P. Snutch, H. E. Olsen, and M. A. R. Consortium, "MinION analysis and reference consortium: Phase 2 data release and analysis of R9. 0 chemistry," F1000Research, vol. 6, 2017.
JEDEC, "JESD235: High Bandwidth Memory (HBM) DRAM," 2013.
G. Kim, J. Kim, J. H. Ahn, and J. Kim, "Memory-centric system interconnect design with hybrid memory cubes," in Proceedings of the 22nd International Conference on Parallel Architectures and Compilation Techniques. IEEE Press, 2013, pp. 145-156.
J. S. Kim, D. Senol Cali, H. Xin, D. Lee, S. Ghose, M. Alser, H. Hassan, O. Ergin, C. Alkan, and O. Mutlu, "GRIM-Filter: Fast seed location filtering in DNA read mapping using processing-in-memory technologies," BMC Genomics, vol. 19, No. S2, p. 89, May 2018.
Y. Kim, W. Yang, and O. Mutlu, "Ramulator: A fast and extensible DRAM simulator," IEEE Computer architecture letters, vol. 15, No. 1, pp. 45-49, 2016.
V. I. Levenshtein, "Binary Codes Capable of Correcting Deletions, Insertions, and Reversals," in Soviet Physics Doklady, 1966.
H. Li, "Aligning sequence reads, clone sequences and assembly contigs with BWA-MEM," arXiv preprint arXiv: 1303.3997, 2013.
H. Li, "Minimap2: pairwise alignment for nucleotide sequences," Bioinformatics, vol. 34, No. 18, pp. 3094-3100, 2018.
J. Liu, H. Zhao, M. A. Ogleari, D. Li, and J. Zhao, "Processing-in-memory for energy-efficient neural network training: A heterogeneous approach," in MICRO, 2018.
Y. Liu and B. Schmidt, "GSWABE: Faster GPU-accelerated sequence alignment with optimal alignment retrieval for short DNA sequences," Concurrency Computation, 2015.
Y. Liu, A. Wirawan, and B. Schmidt, "CUDASW++ 3.0: accelerating Smith-Waterman protein database search by coupling CPU and GPU SIMD instructions," BMC Bioinformatics, vol. 14, No. 1, p. 117, Dec. 2013.
N. Muralimanohar, R. Balasubramonian, and N. Jouppi, "Optimizing NUCA organizations and wiring alternatives for large caches withCACTI 6.0," in Proceedings of the 40th Annual IEEE/ACM International Symposium on Microarchitecture. IEEE Computer Society, 2007, pp. 3-14.
Nai, R. Hadidi, J. Sim, H. Kim, P. Kumar, and H. Kim, "GraphPIM: Enabling Instruction-Level PIM Offloading in Graph Computing Frameworks," in HPCA, 2017.
G. Navarro, "A Guided Tour to Approximate String Matching," ACM Computing Surveys (CSUR), 2001.
S. B. Needleman and C. D. Wunsch, "A General Method Applicable to the Search for Similarities in the Amino Acid Sequence of Two Proteins," Journal of Molecular Biology, 1970.
Y. Ono, K. Asai, and M. Hamada, "PBSIM: PacBio reads simulator-toward accurate genome assembly," Bioinformatics, vol. 29, No. 1, pp. 119-121, 2012.

* cited by examiner

GENOME SEQUENCE ALIGNMENT SYSTEM AND METHOD

BACKGROUND

The present disclosure generally relates to genome sequences and, more particularly, to genome sequence alignment.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

Genome sequencing involves determining a deoxyribonucleic acid (DNA) sequence the physical order for four bases (e.g., guanine, adenine, thymine, and cytosine) found in an organism. The bases may be referred to by their first letter, e.g., G, A, T, C. Biological-based processes may be used to extract and to collect fragments of the organism's DNA sequence and then to assemble the fragments into a complete genome. Each fragment, which may be referred to as a read, may contain multiple bases. Certain short-read technologies, such as high-throughput sequencing, may collect around 200 DNA base pairs, while long-read technologies may generate longer DNA base pairs (e.g., 10,000 base pairs or more). Genome sequencing may include the use of read mapping. In read mapping, extracted fragments may be assembled into a whole genome using a reference genome (e.g., a known complete DNA genome for a particular organism). For example, the extracted fragments may be matched against the reference genome to identify potential locations for each fragment. However, the bases in a read may not be identical to the bases in the reference genome at the original location due to, for example, errors being introduced into the read during fragment extraction. Genome sequence alignment (e.g., read alignment) may be used to identify potential matches for locations of the reads in the reference genome. This process may consume a substantial amount of time and processing resources in software running on a computer.

DETAILED DESCRIPTION OF SPECIFIC EMBODIMENTS

Figure 1:
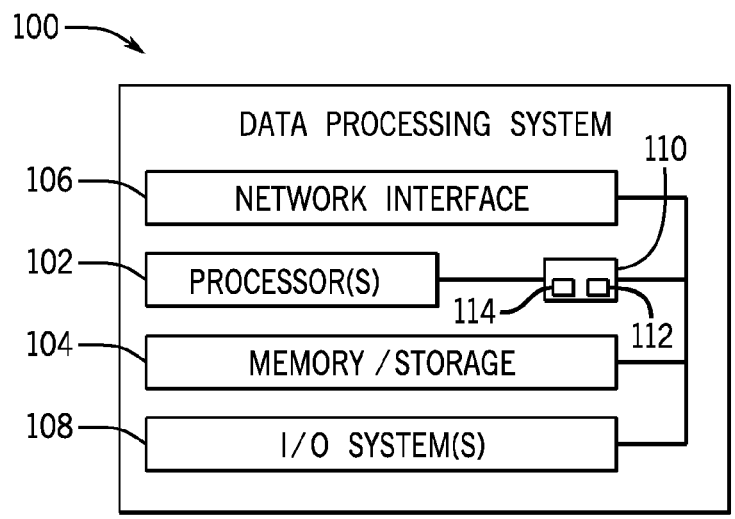
FIG. 1 is a block diagram of a data processing system including one or more processors having genome sequence alignment accelerator circuitry, in accordance with an embodiment of the present disclosure.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present disclosure, the articles "a," "an," and "the" are intended to mean that there are one or more of the elements. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features. Furthermore, the phrase A "based on" B is intended to mean that A is at least partially based on B. Moreover, unless expressly stated otherwise, the term "or" is intended to be inclusive (e.g., logical OR) and not exclusive (e.g., logical XOR). In other words, the phrase A "or" B is intended to mean A, B, or both A and B.

The systems and methods described herein include certain genome sequencing techniques useful in improving genome analysis. In genome sequencing, a deoxyribonucleic acid (DNA) sequence—a physical order for four bases (e.g., guanine, adenine, thymine, and cytosine) of a given organism—may be determined. For example, certain biological-based processes may extract and to collect fragments of the organism's DNA sequence and use the fragments to derive a complete genome. Each fragment, referred to herein as a read, may contain multiple bases. Certain short-read technologies, such as high-throughput sequencing, may collect around 200 DNA base pairs, while long-read technologies, such as Oxford Nanopore Technology (ONT), Pacific Biosciences' (PacBio) Single Molecule, and Real-Time (SMRT) sequencing technology, may generate longer DNA base pairs (e.g., 10,000 base pairs or more).

Read mapping may then be used to further derive the complete genome. During read mapping, the extracted fragments may be assembled into a whole genome by using a reference genome for the organism. The reference genome is a known and complete DNA genome for the organism being analyzed. For example, the extracted fragments (e.g., reads) may be string-matched against the reference genome to identify potential locations for each fragment. However, the bases in a read may not be identical to the bases in the reference genome at the original location due to, for example, errors being introduced into the read during extraction. In some cases, such as for long-read cases, the error rates may be 15% or more.

The systems and methods describe herein include the use of a bit vector-based in-memory accelerator (BitMAC) that uses a modified hardware-based Bitap algorithm. The Bitap algorithm is a fuzzy string-matching algorithm that may use relatively fast and simple bitwise operations to identify potential read matches. The modified Bitap algorithm described herein may now support both short and long reads, and loop-carried data dependencies may be reduced or eliminated so that a single search may be parallelized. BitMAC may also include an algorithm for traceback, which can directly use bit vectors that the modified Bitap algorithm generates to identify a more optimal alignment. The traceback algorithm may use a divide-and-conquer approach for improved efficiency of execution. Indeed, BitMAC may apply parallel bitwise computation units that may make use of processing-in-memory (PIM) to deliver higher memory bandwidth, as further described below.

With the foregoing in mind, FIG. 1 is a block diagram of a data processing system 100 including one or more processor(s) 102, in accordance with an embodiment of the present disclosure. The data processing system 100 may include more or fewer components (e.g., electronic display, user interface structures, application specific integrated circuits (ASICs)) than shown. The data processing system 100 may execute certain code or computer instructions via the or more processors 102, such as an INTEL® 10$^{th}$ generation processor (e.g., Ice Lake processor) that may manage data processing requests for the data processing system 100 (e.g., to perform genome analysis, machine learning, video processing, voice recognition, image recognition, data compression, database search ranking, bioinformatics, network security pattern identification, spatial navigation, or the like).

The processor(s) 102 may communicate with the memory and/or storage circuitry 104, which may be a tangible, non-transitory, machine-readable medium, such as random-access memory (RAM), read-only memory (ROM), one or more hard drives, flash memory, or any other suitable optical, magnetic or solid-state storage medium. The memory and/or storage circuitry 104 may hold data to be processed by the data processing system 100, such as processor-executable control software, configuration software, system parameters, configuration data, etc.

The data processing system 100 may also include a network interface 106 that allows the data processing system 100 to communicate with other electronic devices. In some embodiments, the data processing system 100 may be part of a data center that processes a variety of different requests. For instance, the data processing system 100 may receive a data processing request via the network interface 106 to perform machine learning, video processing, voice recognition, image recognition, data compression, database search ranking, bioinformatics, network security pattern identification, spatial navigation, or some other specialized task. The data processing system 100 may also include one or more input/output systems 108, such as display devices (e.g., computer monitors), keyboards, mice, speakers, voice input devices, and so on, useful for entering and/or displaying information.

In the depicted embodiment, the processor 102 may be operatively and/or communicatively coupled to a bit-vector-based in-memory accelerator (BitMAC) system 110. The BitMAC system 110 may include an in-memory read alignment accelerator for both short reads (e.g., reads of less than 500) and long reads (e.g., reads of 1,000 or more). The BitMAC system 110 may implement a modified Bitap algorithm that may be designed to take advantage of a high internal bandwidth available in certain memories, such as 3-dimentional (3D)-stacked dynamic random access (DRAM) chips. The BitMAC system 110 is flexible insofar as it may perform alignment either on an entire reference genome, or on candidate locations generated by a pre-alignment filter. The BitMAC system 110 may additionally include processing-in-memory (PIM). PIM may take advantage of memory chip design to embed logic in or near the memory. For example, both High-Bandwidth Memory (HBM) and Hybrid Memory Cubes (HMCs) are 3D-stacked DRAM chips that include a logic layer in the chip. The logic layer is internally connected to the memory layers, allowing PIM logic (e.g., BitMAC algorithms) that are implemented in the logic layer to exploit the high memory bandwidth available inside the chip (e.g., the internal bandwidth of HBM may be 8 times the external bandwidth available to CPUs). PIM may improve performance and energy efficiency over traditional CPU-based or GPU-based compute, as PIM may provide higher bandwidth while avoiding less efficient movement of data between DRAM and the CPU/GPU.

The BitMAC system 110 may include two subsystems or components that implement certain modified algorithms. A first subsystem, a BitMAC distance calculator system (BitMAC-DC) 112, may perform distance calculation using a modified Bitap algorithm and may generate bit vectors encoded with information about potential matches and edits. In certain embodiments, the BitMAC-DC 112 may be implemented as a systolic array, which may then enable certain techniques to pipeline multiple iterations of read alignment in a single accelerator. The BitMAC-DC 112 may be further optimized for use with a pre-alignment portion of the process that filters out unlikely match locations for each read. However, the BitMAC-DC 112 may be used for computing the edit distance between the whole reference genome and the input reads, or for finding candidate match regions of the reference genome for any read. A second subsystem, a BitMAC traceback system (BitMAC-TB)114, may implement a Bitap-compatible traceback algorithm. The BitMAC-TB 114 may divide a matching region of the reference genome (as identified by an optional, initial filtering portion of the process) into multiple windows. In some cases, the BitMAC-TB 114 may use a relatively small, relatively low-power, general-purpose PIM core to perform traceback on each window, as further described below.

Figure 2:
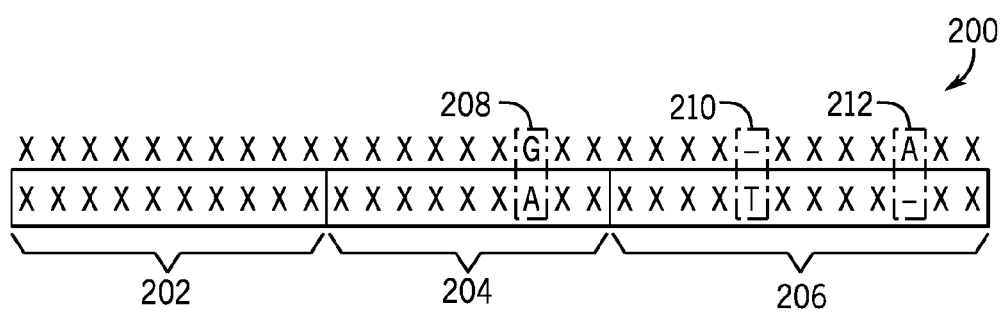
FIG. 2 is a diagram of an example of a reference alphabet (e.g., genome) and certain edits and matches that may be provided by the techniques described herein, in accordance with an embodiment of the present disclosure.

It may be beneficial to describe genome sequencing and certain process that may be used for deriving a complete genome from multiple fragments. Turning now to FIG. 2, the figure illustrates a reference genome 200 that may be used for genome sequencing via read matching. DNA sequencing determines the specific order of nucleotides on a DNA fragment, e.g., the order of G, A, T, C bases. The locations of sample fragments, such as fragments 202, 204, and 206, on the whole genome are usually random. Thus, the sequences of DNA fragments or reads may be organized and combined to form the original longer sequence by applying a genome assembly process. The genome assembly process may be used to create a computational representation of a complete DNA for further data analysis. In FIG. 2, the letter "X" is shown where the nucleotides of the reference genome 200 and the sample fragments 202, 204, and 206 are the same as one another (e.g., G and G, A and A, T and T, C and C). FIG. 2 also shows edits at points where the nucleotides of the reference genome 200 and the sample fragments 202, 204, and 206 are not the same, such as at points of substitution 208, insertion 210, and deletion 212.

At least two types of genome assembly mechanisms may be used: (1) a mechanism that assembles the reads without a template reference sequence (i.e., de novo assembly), and (2) a read mapping mechanism that assembles the reads with respect to the reference sequence. In de novo genome assembly, first, all pairwise read alignments or suffix-prefix matches between each pair of reads, called read-to-read overlaps, may be found. A consensus of these overlapped reads with no gaps may be used to compose contiguous segments (i.e., contigs), which are then combined to regenerate the whole sequence. To decrease the number of alignments between each pair of reads, initial indexing and filtering portions of the process may applied to find candidate overlap locations.

In read mapping, the species of the subject's genome is known, and a reference genome is also known for that species. All of the query reads may be first mapped to the reference genome, and then using these mappings of reads, the original whole sequence may be regenerated. Similar to de novo assembly, in order to decrease the number of alignments between the reference genome and the query reads, initial indexing and filtering portions of the process may be applied to find the candidate mapping locations. For both the de novo and read mapping approaches, alignment portions of the process may be executed with the candidate locations only or with the candidate locations plus some additional locations, instead of using all possible locations. The alignment portions of the process of both read mapping and read-to-read overlap detection may be computationally interpreted as string comparisons which inherit approximate string matching techniques having a predetermined error threshold.

The goal of approximate string matching is to detect the differences and similarities between two genomic sequences. Given a query read sequence $R=r1, r2, \ldots, rn$, a reference segment $F=f1, f2, \ldots, fm$ (where $n \leq m$), and an edit distance threshold E, the approximate string matching problem is to identify a set of approximate matches of R in F (allowing for at most E differences). Read sequences may be prone to sequencing errors by around 0.1% in short reads and around 15% in long reads. Commonly-allowed differences, referred to as edits, include deletions, insertions, and substitutions of characters in one or both sequences. FIG. 2 shows embodiments of each possible kind of edit. For example, a substitution 208 is shown, where base G of the reference genome 200 is substituted with base A. An insertion 210 is further shown, with base T inserted. A deletion 212 is additionally shown, with base A deleted. A match is also shown, where read 202 is matching with a corresponding section of the reference genome 200. To tolerate a deleted character or an inserted character in one sequence compared to another, all possible prefixes (e.g., substrings that include the first character of the string) of the two input sequences may be examined and the pairs of prefixes that provide the largest number of matches may be tracked. This examination and tracking approach may be implemented as a dynamic programming algorithm to avoid re-examining the same prefixes multiple times. Existing implementations, such as Levenshtein distance, Smith-Waterman, and Needleman-Wunsch, may typically have quadratic time and space complexity (i.e., $O(m^2)$ for a sequence length of m characters).

Approximate string matching techniques may not only determine the minimum number of edits between two genomic sequences, but may also provide the location and type of each edit (e.g., substitution 208, insertion 210, and deletion 212). As any two sequences could have a large number of different possible arrangements of the edit operations and matches (and hence different alignments), the approximate string-matching algorithm usually involves a backtracking portion of the process. This backtracking portion of the process may find the combination of edit operations that has the highest alignment score (called optimal alignment). This combination can be represented with a Compact Idiosyncratic Gapped Alignment Report (CIGAR) string, which is a list of pairs of numbers and characters. Each pair consists of a number followed by a character that indicates the associated operation (deletion, insertion, substitution, or match). The number indicates the number of times the corresponding operation must be applied. An alignment score is the sum of the scores of all edits and matches along the alignment, as defined by a user-specified scoring function. In a typical system, alignment may involve significant movement of data between the off-chip memory system and the on-chip compute units that perform the approximate string match. As a result, the off-chip memory bus access may become a bottleneck. The techniques described herein may avoid memory bus bottlenecks by employing 3D-stacked DRAM, which may enable computation to occur physically near the memory where the data resides, thus enabling high bandwidth and low latency.

Figure 3:
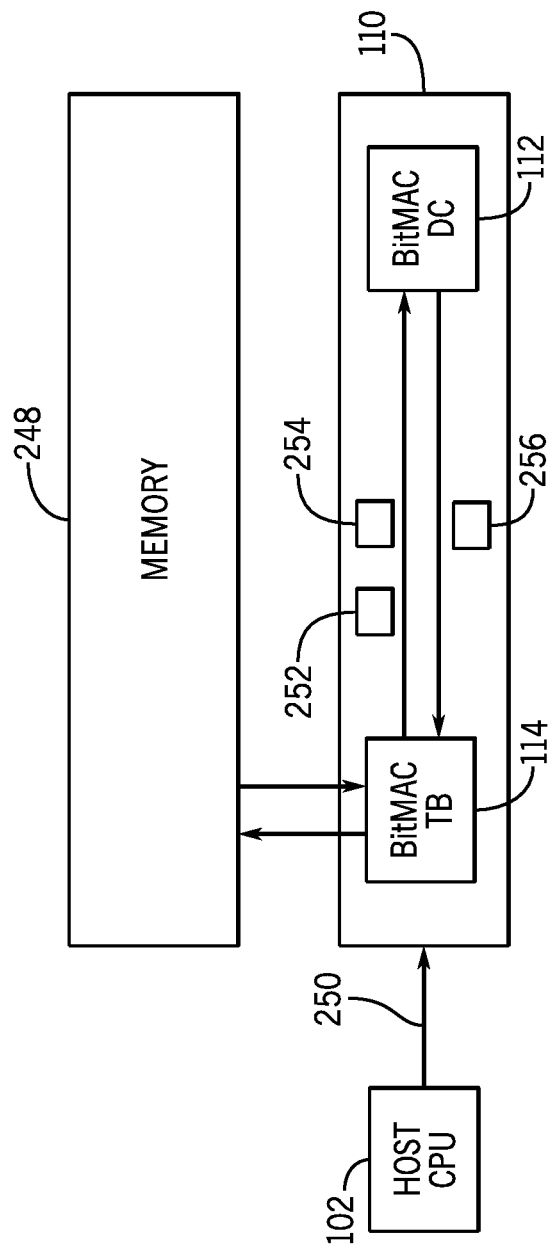
FIG. 3 is a block diagram illustrating a system architecture for bit vector-based accelerator circuitry, in accordance with an embodiment of the present disclosure.

FIG. 3 is a block diagram illustrating a system architecture for an embodiment of the BitMAC system 110. In the depicted embodiment, the BitMAC system 110 is shown as including the BitMAC-DC 112 and the BitMAC-TB 114. In certain embodiments, each vault logic layer in a 3D-stacked memory 248 may contain the BitMAC-DC 112 and the BitMAC-TB 114. During read mapping, the host processor 102 may execute a pre-alignment filter, such as Minimap2's minimizer-based filtering. The pre-alignment filter may generate candidate locations 250 in the reference genome 200 for each read fragment (e.g., fragments 202, 204, 206). For each candidate location 250, the host processor 102 may issue a task to the memory vault containing that candidate location 250, and the BitMAC-TB 114 located at the vault's logic layer may divide the reference genome 200 at the candidate location 250 into multiple overlapping windows.

For each window, the BitMAC-TB 114 may transmit a sub-text 252 (e.g., the portion of the reference genome in one window) and a sub-pattern 254 (e.g., a portion of the read that fits in the one window) to the BitMAC-DC 112. The BitMAC-DC 112 may search for the sub-pattern 254 within the sub-text 252 and generate certain bit vectors 256 (e.g., a vector or array where each element is a bit). In certain embodiments, for each read fragment (e.g., fragments 202, 204, 206) the BitMAC-DC 112 may generate one or more bit vectors 256 (e.g., traceback bit vectors) that record potential edits for the fragment and additionally calculate the minimum edit distance E. The BitMAC-DC 112 may then transmit the bit vectors 256 to the BitMAC-TB 114 once the search is complete. The BitMAC-TB 114 may store the bit vectors 256 in the memory 248.

Once the BitMAC-DC 112 has searched for all sub-patterns 254 within the current window, the BitMAC-TB 114 may read all of the bit vectors generated for the window from memory 248 and generate the window's traceback output. Once the BitMAC-TB 114 generates this output, it moves onto the next window. A design for the BitMAC-TB 114 may exploit a high memory bandwidth available in 3D-stacked memory 248, and, in some embodiments, the BitMAC-TB 114 hardware is placed in the memory's logic layer. While BitMAC-DC 112 may not use a significant memory bandwidth, the BitMAC-DC 112 may communicate more frequently and may be more tightly coupled with the BitMAC-TB 114, and so the BitMAC-DC 112 hardware may be placed in the memory 248 as well.

A modified BitMAC-DC algorithm as implemented by the BitMAC-DC 112 may be highly parallelizable and may perform simple and regular bitwise operations. Accordingly, the BitMAC-DC 112 may be implemented, in certain embodiments, as a systolic array-based accelerator. The BitMAC-TB 114 may use irregular control flow and may perform frequent memory operations. Accordingly, the BitMAC-TB 114 may be implemented, in certain embodiments, as a low-power general-purpose core. While the BitMAC system 110 is envisioned to be used for read mapping, the BitMAC system 110 may also be used to accelerate a read-to-read overlap finding portion of the process of de novo assembly. When used for de novo assembly, the following differences may be found: (1) instead of using a reference text (e.g., genome sequence 200), a full set of reads are indexed and filtered, (2) candidate regions from the pairs of reads are aligned, and (3) traceback is not performed.

An example pseudocode implementation of the algorithm executed via the BitMAC-DC 112 may be as follows:

```
Line 1:     n ← length of text
Line 2:     m ← length of pattern
Line 3:     k ← max edit distance
Line 4:     procedure PRE-PROCESSING
Line 5:         PM ← generatePatternBitmaskACGT(pattern)
Line 6:         for d in 0:k do
Line 7:             R[d] ← 111..111 //initialize R bit vectors with 1s
Line 8:     procedure EDIT DISTANCE CALCULATION
Line 9:         for i in (n-1):0 do
Line 10:            curChar ← text[i]
Line 11:            for d in 0:k do
Line 12:                oldR[d] ← R[d] //copy R to oldR
Line 13:            curPM ← PM[curChar]
Line 14:            R[0] ← (oldR[0]<<1) | curPM //exact match
Line 15:            for d in 1:k do
Line 16:                deletion ← oldR[d-1]
Line 17:                substitution ← (oldR[d-1]<<1)
Line 18:                insertion ← (R[d-1]<<1)
Line 19:                match ← (oldR[d]<<1) | curPM
Line 20:                R[d] ← del & subs & ins & match
Line 21:            if MSB of R[k] == 0 //most significant bit (MSB)
Line 22:                startLoc ← i
Line 23:                editDist ← k
Line 24:                for t in k-1:0 do
Line 25:                    if MSB of R[t] == 0
Line 26:                        editDist ← t
Line 27:                    else
Line 28:                        break
```

In the BitMAC-DC 112 algorithm above, an edit distance (i.e., editDist) between a text (e.g., reference genome) and a query pattern (e.g., read) may be derived with a maximum of k many errors. When k is 0, the algorithm finds the exact matches. The BitMAC-DC 112 algorithm can support the ability to search longer reads and additionally provides parallelism by dividing the input text into overlapping sub-texts and searching the sub-texts in parallel. An overlap (e.g., read overlap) may ensure that possible matches that may fall at the edges of a sub-text are not missed. To guarantee no misses, the overlap may be of length m+k, where m is the length of pattern and k is the maximum number of allowed errors. The BitMAC-DC 112 algorithm embodiment listed above may start with a pre-processing procedure that converts the pattern into m-sized pattern bitmasks, referred to as PM. One pattern bitmask for each character in the alphabet may be generated, and PM[a][i]=0 if and only if pattern[i]=a, where a is a character from the alphabet (e.g., G, A, T, C). These pattern bitmasks may help represent the patterns in a binary format and take advantage of bit-parallelism while computing the edit distance.

When the pattern length is larger than the word size (w) of the machine (e.g., processor 102), the pattern bitmasks are divided into multiple words and to represent an m-sized pattern, $\lceil m/w \rceil$ w-bit words may be used. After the bitmasks are prepared for each character, the bits of state vectors R[d] are initialized to 1s, where d is the current edit distance in range [0; k] (e.g., Lines 6-8). It is to be noted that the algorithm above uses 1's instead of 0's to denote false. That is, instead of logical false being stored as a 0, the algorithms herein store the logical false as a 1, and the logical true as a 0. The first bit vector, R[0], shows the status for an exact match. Likewise, the state vector of the previous iteration with edit distance d is stored in oldR[d] (e.g., Lines 12-14) to take approximate matches into consideration in the next states. At each text iteration, the bitmask of the current character (e.g., curPM) on the text is retrieved (e.g., Line 15). R[0] and all other status vectors of edit d for the three possible error types i.e., deletion, insertion, and substitution, as well as for the match case are computed by applying certain rules (e.g., Lines 19-22) included the BitMAC-DC 112 algorithm, which may in some embodiments only use bitwise OR and shift operations. These four vectors of edit d (Line 21) are processed with a bitwise AND operation to arrange R[d]. By performing a left shift operation at each portion of the process, the current information of a match is moved to the next state's vector.

After computing all state vectors fork errors, if there is a match starting at position i in the text with an edit distance d, 0 may be found at the most significant bit (MSB) of the R[d] bit vector. The traversal of the text may then continue until all possible match positions are examined and the minimum edit distance d is found. When the pattern is longer than the word size, all of the bit vectors need to be stored in multiple words, which may lead to additional computation when performing shift operations. The MSB of the previous word portion of a bit vector may be stored before shifting the previous word. Afterwards, the saved MSB is loaded as the least significant bit (LSB) of the next word for the corresponding bit vector. Thus, the complexity of the algorithm is $\lceil m/w \rceil * m * k$ where m is the pattern length, w is the word size, n is the text length, and k is the edit distance. Due to the simple nature of bitwise operations and low intermediate data storage specification of the BitMAC-DC 112 algorithm listed above, the BitMAC-DC 112 algorithm may be well-suited for hardware acceleration.

It is to be noted that although the BitMAC-DC 112 algorithm listed above is more optimal for genomic sequences, which are composed of only 4 characters (e.g., A, C, G and T), the BitMAC-DC 112 algorithm may be extended to support larger alphabets (e.g., ASCII, Unicode, and so on), and thus provide for a generic text search.

Indeed, in some cases, the only change that may be involved is, when generating the pattern bitmasks at the pre-processing portion of the process (Line 5), instead of generating bitmasks for only 4 characters, the bitmasks may be generated for the full alphabet. In this way, there may be few or no changes to the edit distance calculation portion of the process. It is to be further noted that although the BitMAC-DC 112 algorithm is optimized for edit (e.g., Levenshtein) distance calculation, where each error (i.e., substitution, insertion or deletion) has the same cost (e.g., 1), the BitMAC-DC 112 algorithm can be extended to support different scoring schemas for each error type. For example, when computing the substitution, insertion and deletion bit vectors (Line 19-21), instead of using oldR[d−1] or R[d−1], the BitMAC-DC 112 algorithm may instead use oldR[d−x] or R[d−x], where x is the new cost of the corresponding error.

After finding the matching location of the text and the edit distance with the BitMAC-DC 112 algorithm, a BitMAC-TB 114 algorithm may be used for the traceback portion of the process of alignment. The BitMAC-TB 114 algorithm may find the sequence of matches, substitutions, insertions and deletions, along with their positions for the matched regions, and store these as traceback output. The BitMAC-TB 114 algorithm may use the bit vectors of the BitMAC-DC 112 algorithm, and after a 0-bit is found at one of the R[d] bit vectors' MSB, the BitMAC-TB 114 algorithm follows the found 0 back to the LSB, by reverting the bitwise operations.

An example embodiment, of the BitMAC-TB 114 algorithm may be as follows:

```
Line 1:    curPattern ← 0
Line 2:    curText ← startLoc
Line 3:    errorLeft ← editDist
Line 4:    traceOutput ← ""
Line 5:    while (curPattern < m) & (curText < n) do
Line 6:        endPattern ← min(curPattern+W,m)
Line 7:        endText ← min(curText+W,n)
Line 8:        for i in curText:endText do
Line 9:            for d in 0:min(errorLeft, W) do
Line 10:               start BitMAC-DC to generate bit vectors //
                       Execute BitMAC-DC 112
Line 11:               for pattern[curPattern:endPattern]
Line 12:       patternIndex ← endPattern-curPattern-1 . W-1
Line 13:       textIndex ← 0
Line 14:       curError ← minEditDist from BitMAC-DC
Line 15:       patternConsumed ← 0
Line 16:       while textIndex<(W-O) & patternConsumed<(W-O) do
Line 17:           status ← 0
Line 18:           if match[textIndex][curError ][patternIndex] == 0
Line 19:               status ← 1; add "M" to traceOutput
Line 20:           else if subs[textIndex][curError][patternIndex] == 0
Line 21:               status ← 2; add "S" to traceOutput
Line 22:           else if ins[textIndex][curError ][patternIndex] == 0
Line 23:               status 3 ←; add "I" to traceOutput
Line 24:           else if del[textIndex][curError][patternIndex] == 0
Line 25:               status ← 4; add "D" to traceOutput
Line 26:           if (status > 1)
Line 27:               curError --; errorLeft --
Line 28:           if (status > 0) && (status != 3)
Line 29:               textIndex++
Line 30:           if (status > 0) && (status != 4)
Line 31:               patternIndex --; patternConsumed++
Line 32:       curPattern ← curPattern+patternConsumed
Line 33:       curText ← curText+textIndex
```

The BitMAC-TB 114 algorithm above starts by computing (e.g., with the BitMAC-DC 112 algorithm) all of the intermediate state bit vectors (i.e., match, substitution, deletion, insertion) and by storing all of the intermediate state bit vectors, along with the vectors' ANDed vector, R[d] (Lines 8-15) for the reported text region and also computing the corresponding edit distance from the initial filtering portion of the process. Since the BitMAC-TB 114 algorithm stores all of the intermediate bit vectors, the traces of the 0 at the MSB location may be followed back within each intermediate bit vector and used to generate the traceback output. However, in the worst case, the length of the text region that the query pattern maps may be m+k, assuming all of the errors are deletions from the pattern.

All of the bit vectors for m+k characters are stored, and the BitMAC-TB 114 algorithm computes 4*(k+1) many bit vectors within each text iteration (each m bits long). Accordingly, for long reads with high error rates, the memory used may be on the order of approximately 50 gigabytes (GB). To decrease a memory footprint of the BitMAC-TB 114 algorithm, two techniques may be applied. First, a divide-and-conquer approach may be used. Instead of storing all of the bit vectors for m+k text characters, the text region and the input query may be divided into overlapping windows and he traceback computation may be performed at each window, sequentially. After all of the windows' partial traceback outputs are generated, a merge of the traceback outputs may be applied to find the complete traceback sequence. Although the first approach sacrifices some performance due to the double computation for the overlaps (0 is the overlap size), it helps decrease the memory footprint to W*W*W*4, where W is the window size. This first divide and- conquer technique may also help to reduce the complexity of the bit vector generation via the BitMAC-DC 112 algorithm from m*n*k to W*W*W. Second, instead of storing all 4 bit vectors (i.e., match, substitution, insertion, deletion) separately, the four possibilities may be encoded with 2-bits for each position at each bit vector, and then saving the two bits which encode one of the four corresponding cases. The 2-bit encoding modification may decrease the write bandwidth and the memory footprint from W*W*W*4 to W*W*W*2.

Figure 4:
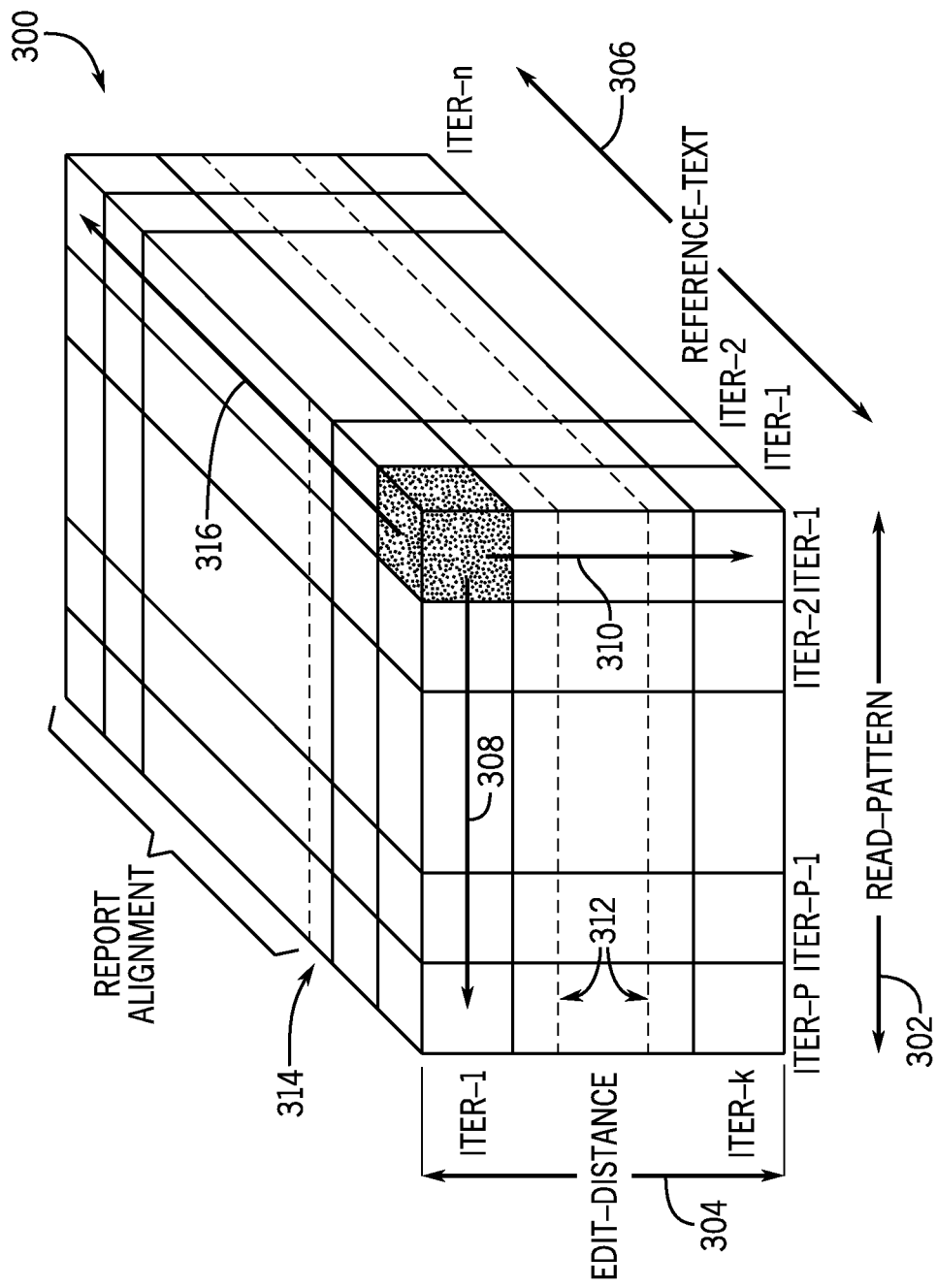
FIG. 4 is a 3-dimensional (3D) block diagram of an embodiment of a walk-through cube that may be used by the bit vector-based accelerator circuitry of FIG. 3, in accordance with an embodiment of the present disclosure.

As mentioned previously, the BitMAC-DC 112 may be implemented in hardware. Turning now to FIG. 4, the figure is a 3-dimensional (3D) block diagram of an embodiment of a walk-through cube 300 that may be used, for example, by a linear cyclic systolic array-based accelerator to implement the BitMAC-DC 112 algorithm. The systolic array-based accelerator may be further optimized to reduce both memory bandwidth and memory footprint. For example, feedback logic enabling cyclic systolic behavior enables the determination of a fixed number of memory ports and a reduction in memory footprint. The systolic array-based accelerator's cubic walk pattern allows execution to be divided into 3 dimensions/iterations, as shown in FIG. 4: A horizontal axis 302 may represent pattern characters, a vertical axis 304 may represent an edit distance, and a depth axis 306 may represents text characters.

The BitMAC-DC 112 may support variable preemption points to reduce energy and to provide for application specific speedup. For example, in read mapping processing, the reference genome (i.e., text) and the read (i.e., pattern) are split into sub-texts and sub-patterns, each iteration of the systolic array-based accelerator may then walk through a small portion of the cube 300, thus more efficiently processing the read(s). In the depicted embodiment, as one moves in a left-to-right direction 308, the read pattern (e.g., bit size) increases in size. Moving from a top-to-bottom direction 310 increases an n in R[n]. As n increases, the errors also increase. For example, n=0 may have no errors, while n=4 may have 4 errors. A breakpoint region 312 may be used to denote when errors may grow too large. That is, outside a bottom of the region 312 errors may be too large for genomic derivations.

Moving in a depth-wise direction 314 increases a pattern length for matching against the reference genome 200. For example, a pattern length boundary 316 may be set for a desired pattern length, e.g., 10,000. As the systolic array-based accelerator moves in the depth-wise direction 314, R[n] becomes OldR[n]. That is, as a cell moves in the depth-wise direction 314 towards the pattern length boundary 316, an immediately previous cell is equivalent to OldR[n]. As noted in the BitMAC-DC 112 and BitMAC-TB 114 algorithms above, fewer R's may be used (e.g., only two R's (e.g., R[x] and OldR[x])) may be used, thus saving memory, as each R includes implicitly previous R derivations. As illustrated, the walk-through cube 300 is suitable for a systolic array implementation, where a cell corresponds to a systolic cell. A resulting systolic array implementation may be cyclic because a first cell in the systolic array may receive inputs from a final cell in the systolic array, as shown in FIG. 5.

Figure 5:
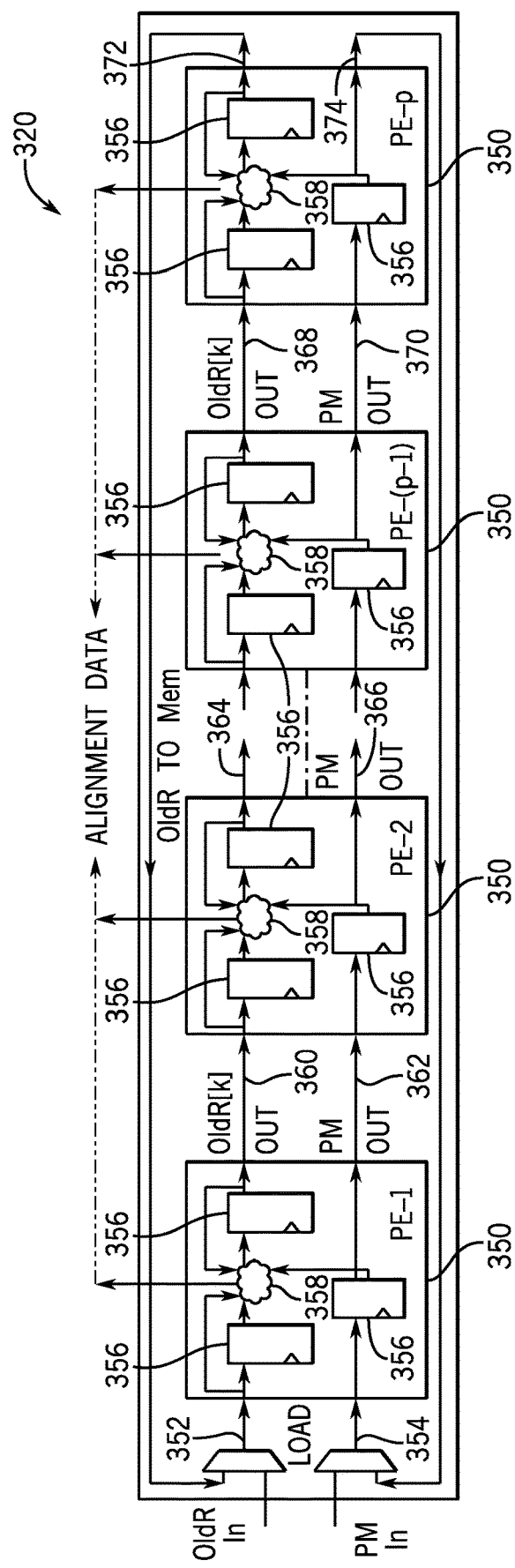
FIG. 5 is a schematic view of a processing block (PB) that may be included in bit vector-based distance counter circuitry, in accordance with an embodiment of the present disclosure.

More specifically, FIG. 5 is a schematic view of an embodiment of a processing block (PB) 320 for the for the BitMAC-DC 112 that may be included in a cyclic systolic array-based accelerator. The PB 320 includes multiple processing elements (PEs) 350 suitable for processing the BitMAC-DC 112 algorithm or portions of the BitMAC-DC 112 algorithm. In the illustrated embodiment, a first PE-1 of the PEs 350 may receive as input 352, 354 either cyclic data from a last PE-p of the PEs 350 or from an external system. The input 352 is representative of an OldR[x] value, while the input 354 is representative of an m-sized pattern bitmask (PM). That is, each PE 350 may be used to compute a pattern match to a w-bit pattern, for example, in accordance to lines 19-23 of the BitMAC-DC 112 algorithm described above.

Each PE 350 may include flip-flops 356 for storage logic, and a processing core 358 for processing certain data as further described below with respect to FIG. 6. In use, the first PE 350, illustrated as PE-1, may receive the inputs 352, 354, and then compute a pattern match (PM) output 360 and also compute OldR[k] output 362. The outputs 360, 362 may then serve as inputs into PE-2, which may then use the inputs to derive outputs 364, 366. The outputs 364, 366 may then be used by the PE 350 downstream of PE-2, and so on. In the depicted embodiment, there are a total of p number of PEs 350. Accordingly, outputs 368, 370 of PE (p−1) are shown as inputs into PE-p. Outputs 372, 374 of the PE-p may be used in a cyclical manner as inputs to the PE-1. For example, because R may depend on OldR computations, the last PE-p's outputs 368, 370 may be used as inputs into the first PE-1. The PB 320 may be used to provide for a more efficient and flexible cyclic systolic array-based accelerator.

Figure 6:
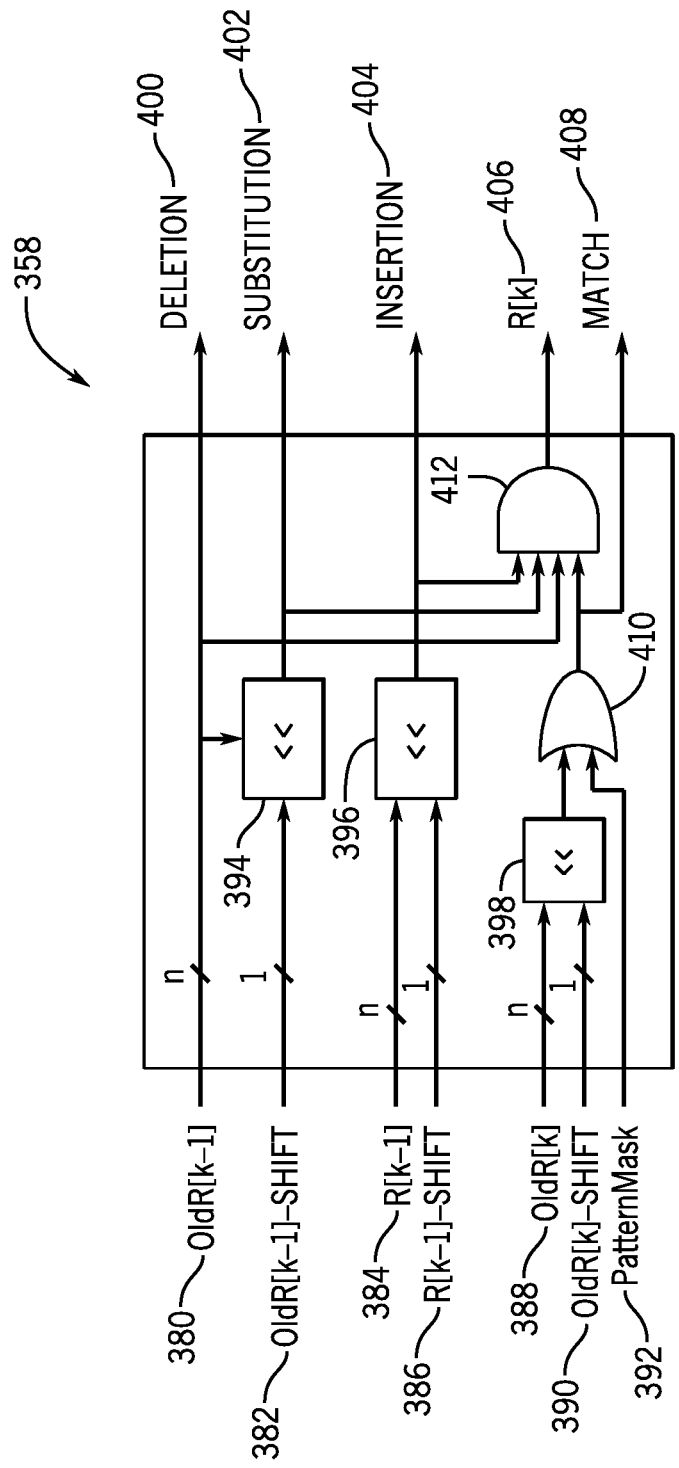
FIG. 6 is a schematic diagram illustrating an embodiment of a processing core that may be included in a processing element (PE) of the PB of FIG. 5, in accordance with an embodiment of the present disclosure.

FIG. 6 is a schematic diagram illustrating an embodiment of the processing core 358 that may be included in each PE 350 of the processing block 320. In the depicted embodiment, the processing core 358 may receive as input an OldR[k−1] value 380, an OldR[k−1]-shift value 382, a R[k−1] value 384, a R[k−1]-shift value 386, an OldR[k] value 388, an OldR[k]-shift value 390, and a pattern bitmask (PM) 392 value. In the depicted embodiment, the processing core 358 may provide for three shift operations via shifters 394, 396, and 398. More specifically, the shifter 394 may left shift the OldR[k−1] value 380 by the amount in the OldR [k−1]-shift value 382. Likewise, the shifter 396 may left shift the R[k−1] value 384 by the amount in the R[k−1]-shift value 386. Similarly, the shifter 398 may left shift the OldR[k] value 388 by the amount in the OldR[k]-shift value 390. In the depicted embodiment, the values 382, 386, and 390 are equal to 1, thus resulting in a single bit shift.

The processing block 320 may output a deletion value 400, a substitution value 402, an insertion value 404, an R[k] value 406, and a match value 408. The deletion value 400, substitution value 402, and the insertion value 404 may be representative of a possible deletion, substitution, and/or insertion, respectively, for a current read being compared against the reference genome 200. The processing block 320 may also include an OR gate 410 and an AND gate 412. The OR gate 410 may receive as input a shifted OldR[k] (e.g., left shift of OldR[k] value 388 by 1 bit) and the pattern bitmask 392 to provide as output the match value 408. The output of the OR gate 410 may be additionally used as one of the inputs into the AND gate 412. As illustrated, the AND gate 412 may then provide the R[k] value output 406.

Figure 7:
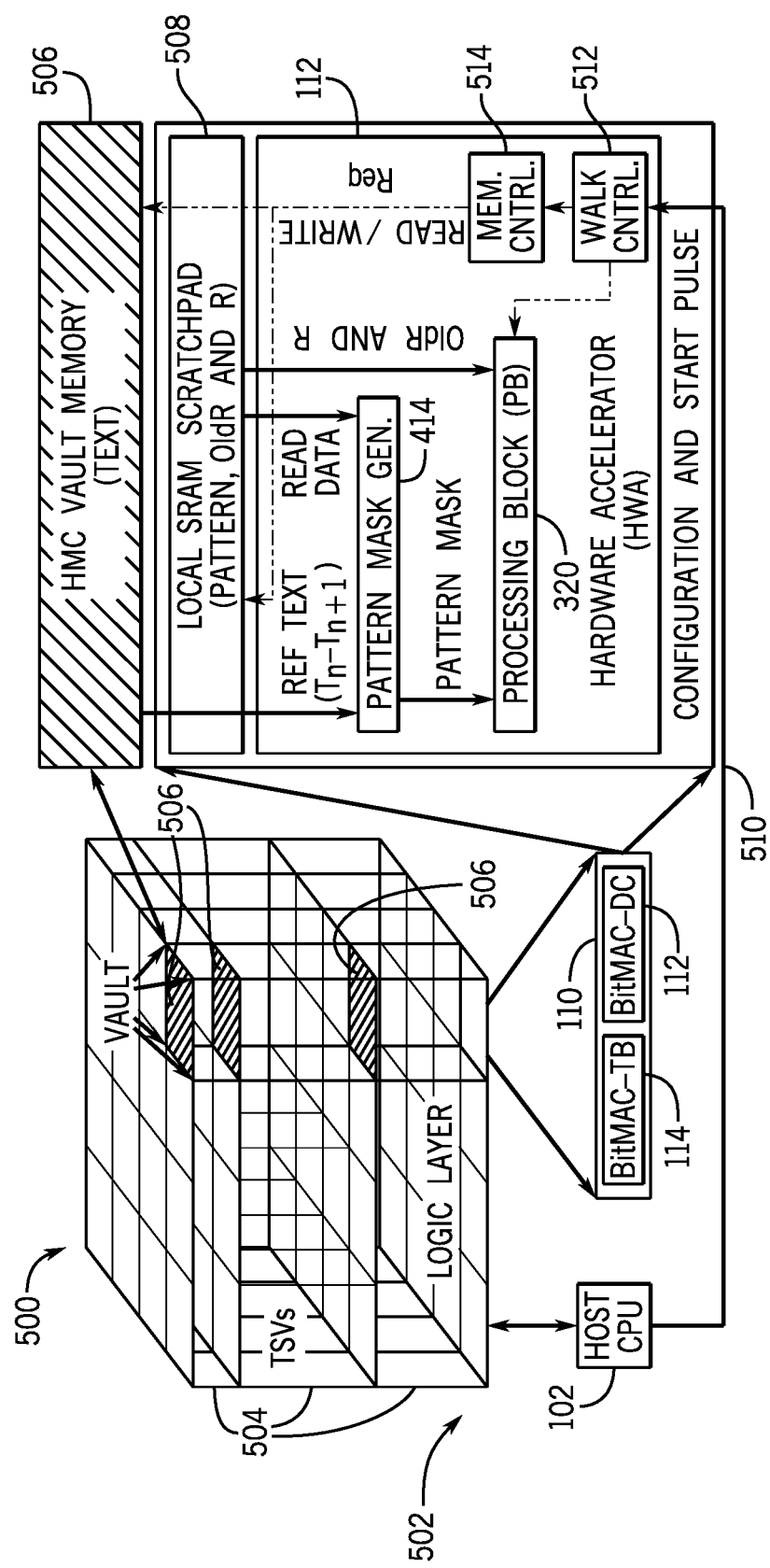
FIG. 7 is a block diagram illustrating an embodiment of the bit vector-based accelerator circuitry of FIG. 3, which may be implemented in a hybrid memory cube (HMC), in accordance with an embodiment of the present disclosure.

FIG. 7 is a block diagram illustrating embodiment of the bit vector-based in-memory accelerator (BitMAC) system 110 which may be implemented in a hybrid memory cube (HMC) 500. More specifically, the figure illustrates the BitMAC system 110 included in a logic layer 502 of the HMC 500. The HMC 500 may consist of a single package or chip containing multiple memory dies and one logic die, stacked together using through-silicon vias (TSVs) 504. Within the HMC 500, memory may be organized into vault memory 506. Each vault memory 506 may be functionally and operationally independent. Each vault memory 506 may include a memory controller in the logic layer 502 that may manage memory reference operations within that vault memory 506.

As shown, the BitMAC-DC 112 may be operatively coupled to a static random access memory (SRAM) 508. During operations, the BitMAC-DC 112 may store certain intermediate results, such as patterns, OldR values, R values, and so on, for example, while moving in the direction 306 of the walk-through-cube 300. For a 64-PE configuration with 64 bits of processing per PE, the BitMAC-DC 112 may use 8 KB SRAM storage for storing intermediate OldR values, the MSB bits for the shift operation, a 10 Kbp-long pattern, and the candidate text region, which may have 11.5 Kbp for the 15% error case. The vault memory 506 may store text, such as the genome sequence 200, and also be operatively coupled to the BitMAC-DC 112.

In use, the host processor (CPU) 102 may provide for configuration information to the BitMAC system 110 and issue a start pulse 510 into a walk control system 512. The walk control system 512 may be operatively coupled to the processing block 320 to implement a "walk" of the walk-through-cube 300, for example via the BitMAC-DC 112 algorithm described above. The walk control system 512 may also be operatively coupled to a memory control system 514 suitable for requesting memory reads and/or writes from the SRAM 508 and the vault memory 506. During the walk, a pattern mask generator 414 system may generate a pattern bitmask (e.g., pattern bitmask 392) to be used as input into to the processing block 320. The pattern bitmask may be based on the reference text (e.g., genome sequence 200) stored in the vault memory 506 and also on intermediate results stored in the SRAM 508).

The processing block 320 may use the pattern bitmask (e.g., pattern bitmask 392) and intermediate values (e.g., OldR, R) during read mapping to generate bit vectors (e.g., bit vectors 256) that record potential edits for the fragment and additionally calculate the minimum edit distance E. More specifically, once the BitMAC-DC 112 has searched for all sub-patterns 254 within a current window, the Bit-MAC-TB 114 may read all of the bit vectors generated for the window from the SRAM 508 and generate the window's traceback output. Once the BitMAC-TB 114 generates this output, the BitMAC-TB 114 may move onto the next window, and so on, until all windows are processed. A Compact Idiosyncratic Gapped Alignment Report (CIGAR) file may then be created, indicating the derived sequence aligns to the reference genome 200.

Figure 8:
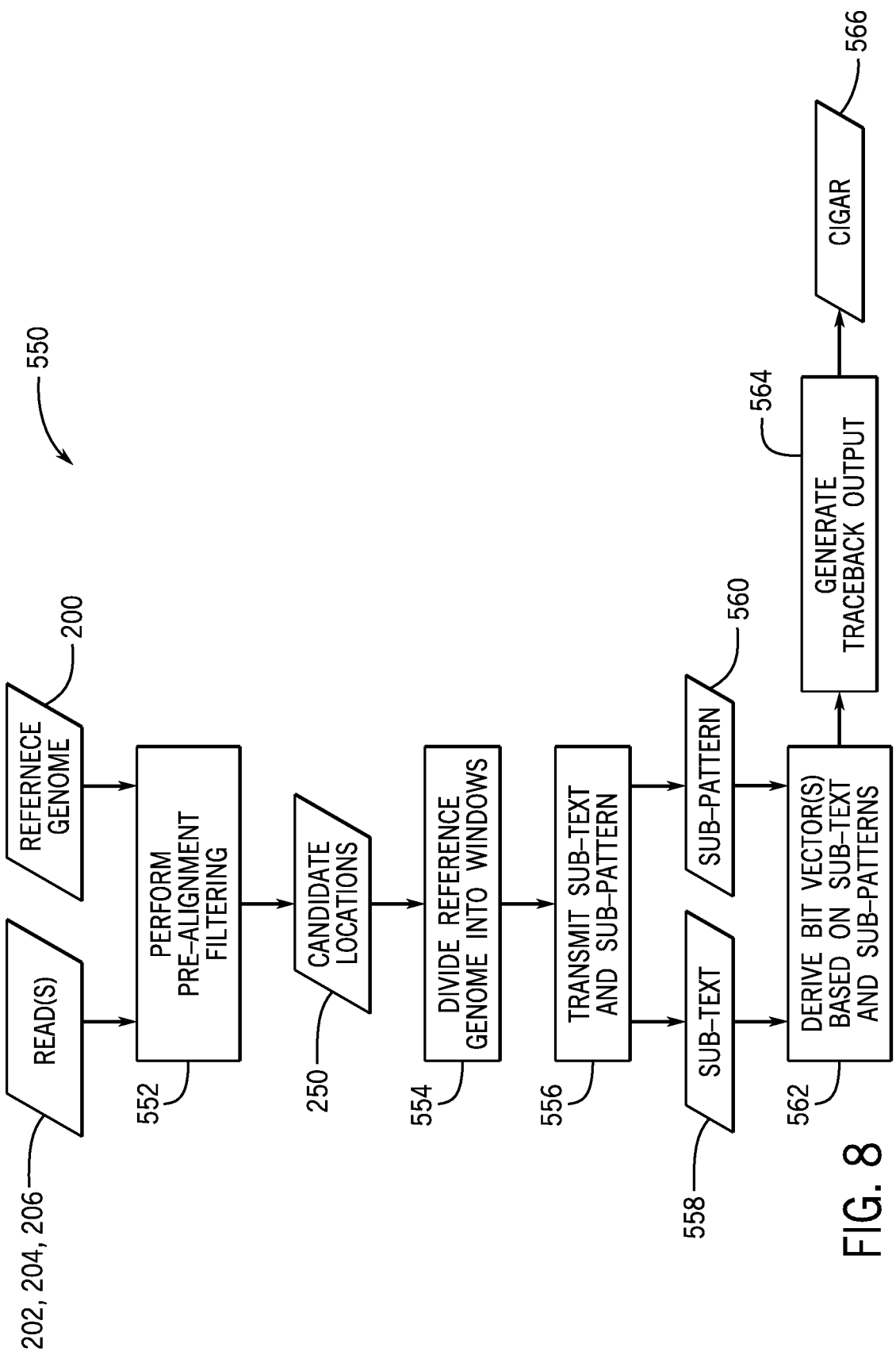
FIG. 8 is a flowchart illustrating a process suitable for read mapping one or more DNA fragments based on a reference genome, in accordance with an embodiment of the present disclosure.

FIG. 8 is a flowchart illustrating an embodiment of a process 550 suitable for read mapping one or more DNA fragments based on a reference genome, such as the reference genome 200. The process 550 may be implemented as computer code or instructions executable via a variety of computing devices such as general purpose microprocessor(s), field programmable gate arrays (FPGA(s)), application specific integrated circuits (ASICs), custom chips, and the like. In certain embodiments, the process 550 may be implemented in certain hybrid memories, such as the HMC 500, via logic layer hardware implementations of the BitMAC-DC 112 and the BitMAC-TB 114.

In the depicted embodiment, the process 550 may receive as input one or more read(s), e.g., reads 202, 204, and 206, and the reference genome 200. The process 550 may then perform (block 552) a pre-alignment filtering. For example, pairwise alignment such as Minimap2's minimized-based filtering may be executed (block 552) to derive one or more candidate locations 250 in the reference genome 200 for each or the reads 202, 204, 206. Minimap2 may be available from the code repository Github. The process 550 may then divide (block 554) the reference genome 200 into one or more windows, including overlap windows (e.g., windows that include neighboring windows' data). For example, the process 550 may execute the BitMAC-TB 114 to divide (block 554) the reference genome 200 into windows as described in the BitMAC-TB 114 algorithm above. For each window, the process 550 may then transmit (block 556) sub-text 558 and/or sub-pattern 560 data, for example, for processing by the BitMAC-TB 114. The sub-text 558 may include a portion of the reference genome 200 based on a window of interest, while the sub-pattern 560 may include a read or a portion of a read, such as the reads 202, 204, 206.

The process 550 may then derive (block 562) bit vector(s) that that record potential edits for the read undergoing analysis and that additionally calculate the minimum edit distance E as described above with respect to the BitMAC-DC 112 algorithm. The process 550 may then use the bit vectors and/or edit distance E to generate (block 564) a traceback output. As mentioned above, the bit vectors and/or edit distance E may be processed by the BitMAC-TB 114 to generate (block 564) traceback output representative of read mappings, e.g., for the reads 202, 204, 206. In certain embodiments, the BitMAC-TB 114 may be included as a software component, for example, of the host processor 102. The process 550 may then create certain reports, such as a CIGAR 566, indicating deletion, insertion, substitution, and/or match operations. In this manner, a more efficient genome read mapping may be provided.

It is to be noted that while the BitMAC-DC 112 and/or BitMAC-TB 114 may be implemented in-memory and/or as software, the BitMAC-DC 112 and/or BitMAC-TB 114 may also be implemented as hardware in non-memory circuitry, such as a field programmable gate array (FPGA), an application specific integrated circuits (ASIC), a processing-in-memory (PIM) circuitry, a High-Bandwidth Memory (HBM) circuitry, a custom microchip, and so on. Accordingly, implementations of the BitMAC-DC 112 and/or BitMAC-TB 114 that include hardware implementations in a FPGA, an ASIC, a PIM circuitry, a logic level included in a HMC, a HBM) circuitry, a custom microchip, or a combination thereof, may be referred to as a bit vector-based distance counter circuitry and as a bit vector-based traceback circuitry, respectively. The BitMAC-DC 112 and/or BitMAC-TB 114 may also be implemented in software executable via a general purpose microprocessor. Accordingly, the software implementations of the BitMAC-DC 112 and/or BitMAC-TB 114 that execute in a general purpose microprocessor circuitry may also be referred to as the bit vector-based distance counter circuitry and as the bit vector-based traceback circuitry, respectively.

Figure 9:
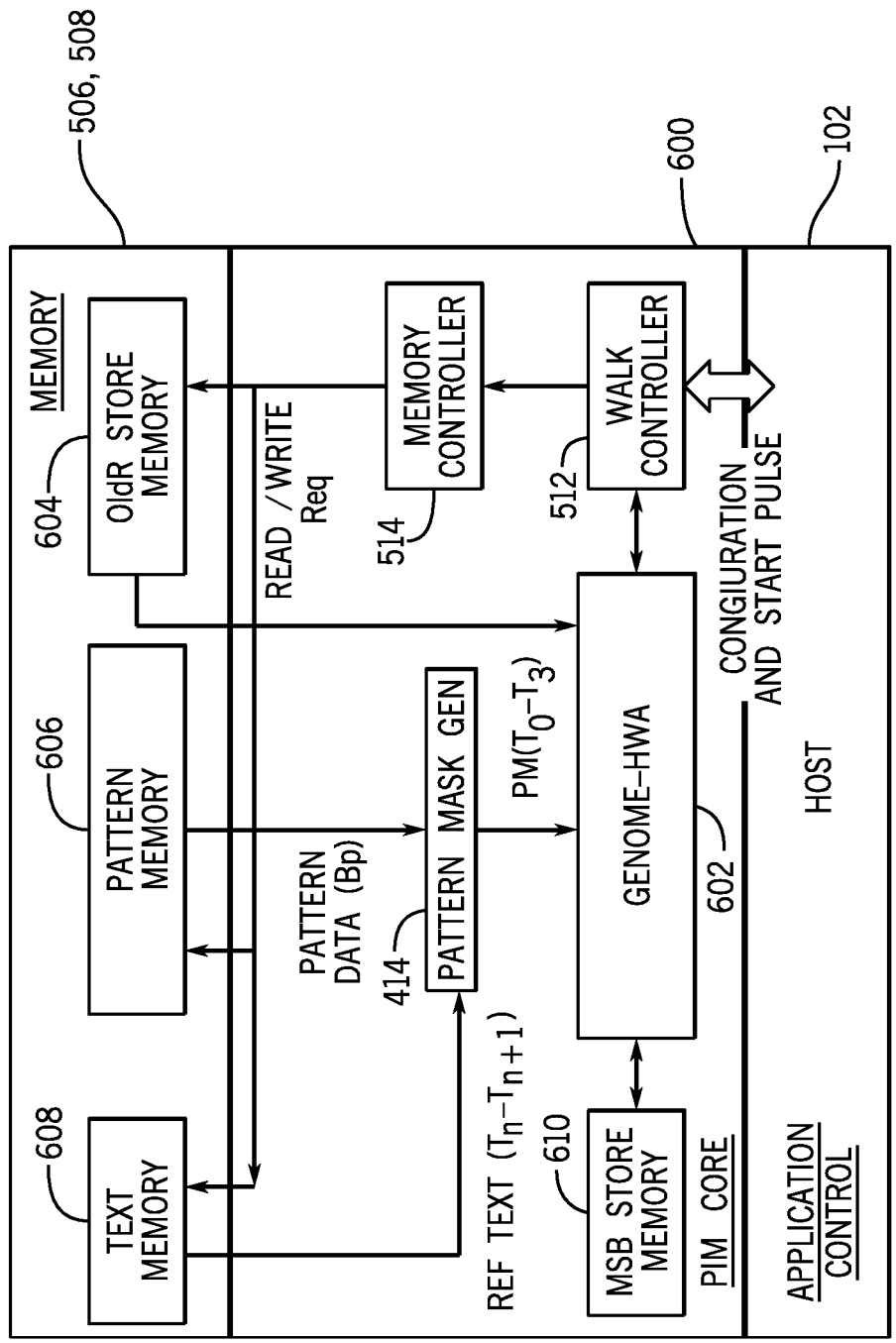
FIG. 9 is a block diagram illustrating a genome hardware accelerator (HWA), in accordance with an embodiment of the present disclosure.

Turning now to FIG. 9, the figure illustrates an embodiment of a PIM circuit or core 600 that may be used to implement the techniques described herein. The PIM core 600 may include a genome hardware accelerator (HWA) 602. For example, the genome HWA 602 may incorporate the processing block 320 having the processing elements 350 suitable for processing the BitMAC-DC 112 algorithm or portions of the BitMAC-DC 112 algorithm described with respect to FIG. 7. In the depicted embodiment, the genome HWA 602 may be operatively coupled to the walk control system 512 to "walk", e.g., process, through the walk-through cube 300 based on a start pulse sent by the host processor 102. That is, the processor 102 may set up the PIM core 600, for example by setting walk parameters such as walk-through cube 300 dimensions, and then issue the start pulse. The walk control system 512 may then communicate with the genome HWA 602 and/or memory controller system 514 to process data, such as walk-through cube 300.

For example, OldR memory 604, pattern memory 606, and/or text memory 608 may be retrieved from certain memory device(s), such as the vault memory 506 and/or the static random access memory (SRAM) 508, and provided to the pattern mask generator 414 and to the genome HWA 602. The genome HWA 602 may use the memory inputs as well as pattern(s) provided via the pattern mask generator 414 to derive deletions, substitutions, insertions, matches, values for R, and the like. The genome HWA 602 may additionally use certain temporary, such as a most significant bit (MSB) store memory 610 depicted in the figure. Accordingly, the genome HWA (e.g., including the processing block 320), may be used to process genomic data.

In certain embodiments, the genome HWA may be used via a processor instruction, such as a "genomax Rref, Rrd, Rout" macroinstruction. That is, an assembly-level macro-instruction may be provided, suitable for performing genome string matching. Operands for the genomax instruction may include a Rref input, representative of a reference data memory location to use, a Rrd input representative of a sting to be matched (e.g., a read location in memory of the string to be matched), and a Rout output, representative of a memory location for output data (or intermediate data) to be saved. Other opcodes, immediate, and/or additional general-purpose register operands may include an RLen, and SLen, and an SStr. The RLen may be representative of the reference length, the SLen may be representative of the read string length, and the SStr may be representative of a start string location (e.g., 0, 1, 2, and so on, of a character array).

The genomax instruction may be implemented in three modes, including an end-to-end execution mode, a preemptable execution mode, and a data chunk operation mode. The end-to-end execution mode may complete execution of the genomax instruction only when all possible alignment results are derived. Accordingly, the preemptable execution mode may have a longer execution time when compared to the preemptable execution mode and to the data chunk operation mode. The preemptable execution mode may include preemption at specific points. For example, if the processor executing the genomax instruction wishes to deliver an interrupt or exception, then an accelerator (e.g., genome HWA 602) state may be "frozen" so the operations may resume at a later time (e.g., after the interrupt or exception). In certain embodiments, the accelerator state may be saved (e.g., context saved) to include execution state, intermediate data values, and so on. The preemptable execution mode may resume execution by calling the same genomax instruction with the appropriate start string value to indicate where execution was stopped previously.

The data chunk operation mode may process partial data sets, e.g., in chunks. For example, a chunk of data may be used, sized to be accommodated via certain processors, such as processors that use INTEL® Advanced Vector Extensions (AVX™). AVX™ processors may use "tiles" or matrices of a given size as part of an execution pipeline, and the chunks may be sized to fit a desired AVX™ tile size. In certain embodiments, a block of the walk-through cube 300 may be sized such that the block may have an edit distance (Y axis) k/c, a text compute distance (Z axis) p, and a pattern compute distance (X axis) P*b where k is a max edit distance, c is an edit distance per chunk, P is the number of processing elements (PEs), and b is the number of bits per PE. Flip-flop-based storage may be used within the genome accelerator 602 to retain values until a subsequent chunk is submitted to the pipeline. The data chunk operation mode may also be preemptable, and a context save/restore technique may be used, as described above with respect to the preemptable execution mode.

When using a compute chunk (e.g., block of the walk-through cube 300 as sized previously) with a 128 PE configuration where each PE suitable for processing 128 bit, 64 edit distances may be computed if the processor includes 1 kilobyte (KB) tile registers. The edit distances may be changed given a different tile register size. The data chunk operation mode may include a version of the genomax instruction that works on partial (e.g. chunked) data. Accordingly, a "partial_genomax Rref, Rrd, Rout" instruction may be provided, which may perform a partial string match on a given chunk of data. An example pseudocode that uses the partial_genomax instruction during partial string matching may be as follows:

Variables: n=length of text, m=length of pattern, k=max edit distance, p=number of processing elements (PEs), b=bits per processing element, and c=edit distance per chunk.

| Line 1: | procedure Edit_Distance Calculation |
| Line 2: | for i in (n -1): 0, i = i − p do |
| Line 3: | for j in 0:m − 1, j = j + b do |
| Line 4: | for d in 0: k, d = d + c do |
| Line 5: | reg0 = load R[d] |
| Line 6: | end for |
| Line 7: | reg 1 = load [current Char, Reference] // load reference text |
| Line 8: | reg0 = partial_genomax [reg0, reg1, reg2] |
| Line 9: | end for |
| Line 10: | end for |
| Line 11: | end procedure |

Figure 10:
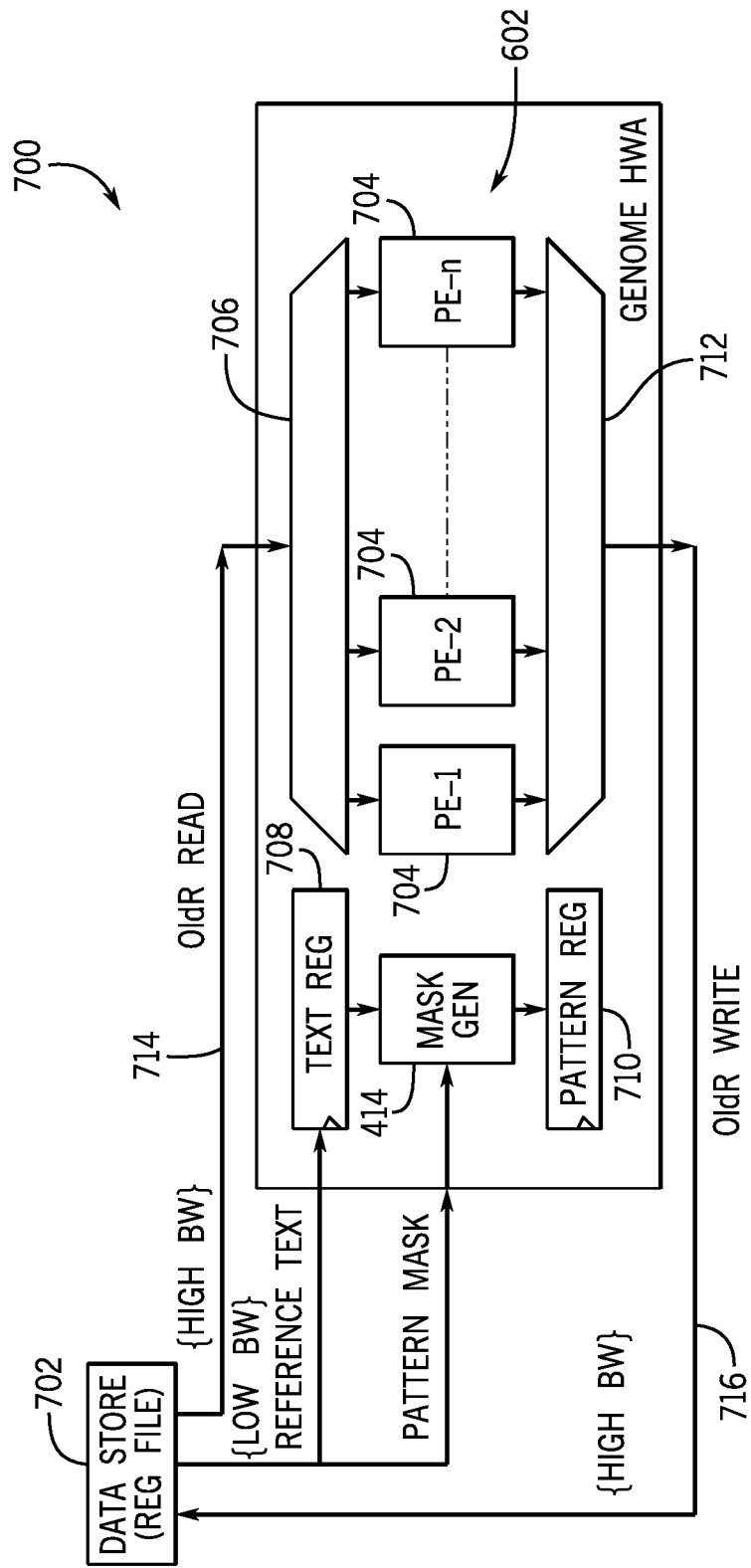
FIG. 10 is a block diagram of a hardware pipeline that may use the genome HWA of FIG. 9.

The genomax and/or partial_genomax instructions may be implemented by using, for example, the genome HWA 602, as shown in in FIG. 10. More specifically, FIG. 10 is a block diagram illustrating an embodiment of a hardware architecture 700 that may be used to implement the genomax and/or partial_genomax instructions. In certain embodiments, the hardware architecture 700 may be provided by INTEL® AVX™ processors. As depicted, the hardware architecture 700 may include a data store 702, such as a registry file (e.g., one or more registers). The data store 702 may be used to provide inputs into the processing elements (PEs) 704, such as the OldR values used by the BitMAC-DC 112. The OldR values may be routed via routing circuitry 706 to all of the PEs 704. The architecture 700 may also include certain registers 708, 710, that may be used to store text and patterns, respectively.

Also illustrated is the pattern mask generator 414, suitable for generating pattern bitmasks such as bitmask 392. Output of the PEs 704 (e.g., derived OldR values) may then be routed to be stored in the data store 702 via routing circuitry 712. In some embodiments, one or more lines 714 used to communicate the OldR values from the data store 702 into the routing circuitry 706 may be read-only lines having high bandwidth, thus providing for a high bandwidth read-only port. In some embodiments, one or more lines 716 used to communicate certain values (e.g., derived OldR values) to the data store 702 may be write-only lines having high bandwidth, thus providing for a high bandwidth write-only port. Text and bitmasks may be communicated at less frequency than OldR values, and thus, lines 718 and 720 used to communicate text and patterns bitmasks respectively, may be lower bandwidth lines when compared to lines 714, 716. Further, lines 714, 716 may be suitable for streaming and prefetching of data. By providing for the hardware architecture 700, such as via INTEL® AVX™ processors, the techniques described herein may implement the genomax and/or partial_genomax instructions in accelerated hardware.

While the embodiments set forth in the present disclosure may be susceptible to various modifications and alternative forms, specific embodiments have been shown by way of example in the drawings and have been described in detail herein. However, it may be understood that the disclosure is not intended to be limited to the particular forms disclosed. The disclosure is to cover all modifications, equivalents, and alternatives falling within the spirit and scope of the disclosure as defined by the following appended claims.

What is claimed is:

1. A system, comprising:
a bit vector-based distance counter circuitry configured to generate one or more bit vectors encoded with information about potential matches and edits between a read and a reference genome, wherein the read comprises an encoding of a fragment of deoxyribonucleic acid (DNA) encoded via bases G, A, T, C; and
a bit vector-based traceback circuitry configured to divide the reference genome into one or more windows and to use the one or more bit vectors to generate a traceback output for each of the one or more windows, wherein the traceback output comprises a match, a substitution, an insert, a delete, or a combination thereof, between the read and the one or more windows.

2. The system of claim 1, wherein the bit vector-based distance counter circuitry comprises a systolic array having a plurality of processing elements.

3. The system of claim 2, wherein each of the processing elements comprises a processing core circuitry configured to receive as input an R array representative of a bit vector, an OldR array representative of a previous bit vector, and a pattern bitmask representative of a sub-pattern included in the read, and to provide as output a potential match, a potential substitution, a potential insert, a potential delete, or combination thereof, between the pattern bitmask and a sub-text of a window of the one or more windows.

4. The system of claim 3, wherein the processing core circuitry comprises at least one shifter and at least one logic gate.

5. The system of claim 2, wherein the systolic array comprises a linear systolic array having the plurality of processing elements connected in a linear manner.

6. The system of claim 5, wherein the linear systolic array comprises a cyclical linear systolic array having a first processing element included the plurality of processing elements disposed first in the cyclical linear systolic array and having a last processing element included in the plurality of processing elements disposed last in the cyclical linear systolic array, wherein the first processing element is communicatively coupled to the last processing element.

7. The system of claim 1, comprising a hybrid memory cube (HMC) circuitry, a High-Bandwidth Memory (HBM) circuitry, or a combination thereof, having at least one logic layer and at least one vault memory, wherein the bit vector-based distance counter circuitry and the bit vector-based traceback circuitry are disposed in the at least one logic layer.

8. The system of claim 1, comprising a host processor (CPU), wherein the bit vector-based distance counter circuitry, the bit vector-based traceback circuitry, or the combination thereof, are included in an accelerator circuitry, wherein the CPU is operatively coupled to the accelerator circuitry to provide for configuration information to execute the bit vector-based distance counter circuitry, the bit vector-based traceback circuitry, or the combination thereof.

9. The system of claim 1, wherein the bit vector-based distance counter circuitry, the bit vector-based traceback circuitry, or a combination thereof, is used to implement a genomax macroinstruction, a partial_genomax macroinstruction, or a combination thereof.

10. The system of claim 1, wherein the bit vector-based distance counter circuitry, the bit vector-based traceback circuitry, or a combination thereof, is included in a hardware accelerator circuitry.

11. A method, comprising:
generating, via a bit vector-based distance counter circuitry, a plurality of bit vectors encoded with information about potential matches and edits between a read and a reference genome, wherein the read comprises an encoding of a fragment of deoxyribonucleic acid (DNA) encoded via bases G, A, T, C;
generating a traceback output comprising a match, a substitution, an insert, a delete, or a combination thereof, between the read and the reference genome based on the plurality of bit vectors; and
generating a report indicating a possible location of the read in the reference genome based on the traceback output.

12. The method of claim 11, comprising performing a pre-alignment to derive one or more candidate locations in the reference genome to analyze based on the read.

13. The method of claim 12, comprising using the candidate locations to divide the reference genome into one or more windows.

14. The method of claim 11, wherein generating the traceback output comprises dividing the reference genome into one or more windows and using the plurality of bit vectors to generate the traceback output for at least one of the one or more windows.

15. The method of claim 11, wherein the report comprises a Compact Idiosyncratic Gapped Alignment Report (CIGAR) file having a number followed by a character that indicates the match, the substitution, the insert, the delete, or the combination thereof.

16. A non-transitory, computer-readable medium storing instructions, wherein the instructions comprise:
a genomax instruction, a partial_genomax instruction, or a combination thereof, that when executed cause circuitry to:
perform a pre-alignment to derive one or more candidate locations in a reference genome based on a read, wherein the read comprises an encoding of a fragment of deoxyribonucleic acid (DNA) encoded via bases G, A, T, C;
generate information about potential matches and edits between the read and the reference genome by deriving a plurality of bit vectors encoded with information about potential matches and edits between the read and the reference genome; and
generate a report indicating a possible location of the read in the reference genome.

17. The non-transitory, computer-readable medium of claim 16, wherein executing the genomax instruction, the partial_genomax instruction, or the combination thereof, comprises providing a bit vector-based distance counter circuitry with the read and the reference genome as input, and wherein the vector-based distance counter circuitry comprises a systolic array.

18. The non-transitory, computer-readable medium of claim 17, wherein executing the genomax instruction, the partial_genomax instruction, or the combination thereof, comprises providing, to a processing element included in the systolic array, an R array representative of a bit vector of the plurality of bit vectors, an OldR array representative of a previous bit vector, and a pattern bitmask representative of a sub-pattern included in the read, wherein the processing element comprises a processing core circuitry configured to receive the R array, the OldR array, and the pattern bitmask, and to provide as output a potential match, a potential substitution, a potential insert, a potential delete, or combination thereof.

19. The non-transitory, computer-readable medium of claim 16, wherein the report comprises a Compact Idiosyncratic Gapped Alignment Report (CIGAR) file based on a traceback output provided by a bit vector-based traceback circuitry, and wherein the bit-vector based traceback circuitry is included in a host processor (CPU), in a hardware accelerator, or in a combination thereof.

20. The non-transitory, computer-readable medium of claim 16, wherein the circuitry comprises a microprocessor, a field programmable gate array (FPGA), application specific integrated circuits (ASIC), a processing-in-memory (PIM) circuitry, a logic level included in a hybrid memory cube (HMC), a High-Bandwidth Memory (HBM) circuitry, a custom microchip, or a combination thereof.

* * * * *